United States Patent [19]

Miller

[11] 4,260,543
[45] Apr. 7, 1981

[54] CRYSTALLINE N-FORMIMIDOYL THIENAMYCIN

[75] Inventor: Thomas W. Miller, Carteret, N.J.

[73] Assignee: Merck & Co., Inc., Rahway, N.J.

[21] Appl. No.: 33,932

[22] Filed: Apr. 30, 1979

Related U.S. Application Data

[63] Continuation-in-part of Ser. No. 921,379, Jul. 3, 1978, abandoned.

[51] Int. Cl.$^3$ ............................................. C07D 487/04
[52] U.S. Cl. ............................... 260/245.2 T; 424/274
[58] Field of Search ..................... 260/326.31, 245.2 T

[56] References Cited

U.S. PATENT DOCUMENTS

| 3,655,656 | 4/1972 | Van Heyningen | 424/246 |
| 4,194,047 | 3/1980 | Christensen et al. | 260/245.2 T |

FOREIGN PATENT DOCUMENTS

848545  5/1977  Belgium ............................... 260/326.31

*Primary Examiner*—Mary C. Lee
*Attorney, Agent, or Firm*—Hesna J. Pfeiffer; Julian S. Levitt; James A. Arno

[57] ABSTRACT

Disclosed is crystalline N-formimidoyl thienamycin and a process for its preparation.

1 Claim, No Drawings

CRYSTALLINE N-FORMIMIDOYL THIENAMYCIN

This application is a continuation-in-part of Ser. No. 921,379, filed July 3, 1978, now abandoned.

BACKGROUND OF THE INVENTION

This invention relates to crystalline N-formimidoyl thienamycin and a process for its preparation.

The antibiotic N-formimidoyl thienamycin (I) is known, see for example, Belgium Pat. No. 848,545 (issued May 20, 1977):

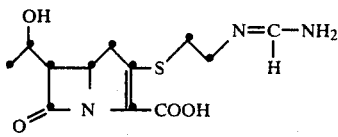

The crystalline form of N-formimidoyl theinamycin which is disclosed and claimed by this application is prepared from a lyophilized sample of I and is found to have unexpected stability in the solid state over the lyophilized form.

DETAILED DESCRIPTION OF THE INVENTION

The description and claimed crystalline N-formimidoyl thienamycin exists as a monohydrate and is unambiguously identified by the following parameters of the crystal which were obtained by X-ray powder diffraction.

| Peak Position | | Intensity | Peak Position | | Intensity |
|---|---|---|---|---|---|
| 2-Θ (CuKα) | d-Spacing (Å) | I/I$_o$ | 2-Θ (CuKα) | d-Spacing (Å) | I/I$_o$ |
| 9.75 | 9.07 | 100 | 26.9 | 3.31 | 75 |
| 11.35 | 7.80 | 40 | 28.7 | 3.11 | 37 |
| 13.85 | 6.39 | 11 | 29.9 | 2.99 | 17 |
| 14.5 | 6.11 | 4 | 30.8 | 2.90 | 7 |
| 15.75 | 5.63 | 14 | 31.85 | 2.81 | 12 |
| 17.5 | 5.06 | 30 | 32.6 | 2.75 | 10 |
| 18.9 | 4.69 | 27 | 32.9 | 2.72 | 10 |
| 19.6 | 4.53 | 12 | 33.4 | 2.68 | 5 |
| 20.0 | 4.44 | 14 | 33.9 | 2.64 | 10 |
| 21.45 | 4.14 | 30 | 34.8 | 2.58 | 26 |
| 21.75 | 4.08 | 36 | 35.6 | 2.52 | 14 |
| 22.3 | 3.98 | 45 | 37.0 | 2.43 | 5 |
| 22.9 | 3.88 | 30 | 38.3 | 2.35 | 9 |
| 23.3 | 3.82 | 28 | 39.3 | 2.29 | 6 |
| 24.3 | 3.66 | 33 | 40.0 | 2.25 | 9 |
| 25.35 | 3.52 | 24 | 42.0 | 2.20 | 14 |
| 25.8 | 3.45 | 20 | 42.4 | 2.14 | 18 |

Crystalline N-formimidoyl thienamycin monohydrate is prepared from a water/ethanol solution of N-formimidoyl thienamycin. The following specific example illustrates the crystallization.

EXAMPLE 1

Crystalline N-formimidoyl Thienamycin

A lyophilized sample of N-formimidoyl thienamycin (62 mg) is dissolved in 1.0 ml of water and diluted with 5.5 ml of 95% ethanol. The resulting solution is immersed in an ice-bath, stirred with a magnetic stirrer and seeded with N-formimidoyl thienamycin monohydrate crystals obtained by a procedure described immediately below. After 1½ hours stirring, the crystals are recovered by centrifugation. After decantation, the crystals are washed with 1 ml of ethanol and dried under vacuum at 50° C. for 1 hour to yield 56 mg of crystalline N-formimidoyl thienamycin monohydrate. The seed crystals employed in the above crystallization are prepared by the following procedure: A lyophilized sample of N-formimidoyl thienamycin (24.5 mg) is dissolved in 0.5 ml of water, diluted to 3.0 ml with ethyl alcohol and stored in the freezer (−5° C.). After two weeks, crystals are observed on the walls of the glass tube.

N-formimidoyl thienamycin is used as an antibiotic, as disclosed in the Belgian Pat. No. 848,545, referred to above. The most current U.S. equivalent of this patent is U.S. Ser. No. 852,425, filed Nov. 17, 1977, now U.S. Pat. No. 4,194,047.

In the treatment of bacterial infections in man, the compound of this invention is administered orally or parenterally, in accordance with conventional procedures for antibiotic administration, in an amount of from about 2 to 600 mg/kg/day and preferably about 15 to 150 mg/kg/day in preferably divided dosage, e.g. three to four times a day. They may be administered in dosage units containing, for example 25, 250, 500 or 1000 mg. of active ingredient with suitable physiologically acceptable carriers or excipients. The dosage units are in the form of liquid preparations such as solutions or suspensions or as solids in tablets or capsules. It will, of course, be understood that the optimum dose in any given instance will depend upon the type and severity of infection to be treated, and the smaller doses will be employed for pediatric use, all of such adjustments being within the skill of the practioner in the field.

In addition to use alone, a particularly preferred method of using N-formimidoyl thienamycin is in combination with a dipeptidase (E.C. 3.4.13.11) inhibitor, as disclosed in an invention commonly assigned, made by Kropp and Kahan, U.S. Ser. No. 927,213 filed July 24, 1978, now abandoned, the contents of which are incorporated by reference.

The class of dipeptidase inhibitor compounds which are claimed separately in U.S. Ser. No. 927,212, filed July 24, 1978, now abandoned, can generally be described by the following formula:

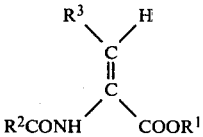

wherein $R^2$ and $R^3$ are hydrocarbon radicals in the range respectively of 3–10 and 1–15 carbon atoms. In either of these hydrocarbon radicals, a hydrogen may be replaced by halogen or a non-terminal methylene may be replaced by oxygen or sulfur, including oxidized forms of the latter. A hydrogen in $R^3$ may also be replaced by a carboxy, alkoxycarbonyl, amido, amidino, cyano, mercapto, and phosphono or amino group. $R^2$ is preferably a branched or cycloalkyl radical ($C_{3-10}$), with a limitation that the carbon adjacent to the carbonyl cannot be tertiary. $R^1$ is hydrogen, loweralkyl ($C_{1-6}$) or dialkylaminoalkyl (e.g., —CH$_2$CH$_2$N(C$_2$H$_5$)$_2$, —CH$_2$CH(CH$_3$)N(CH$_3$)$_2$.

A particularly preferred sub-group of inhibitor compounds are those in which $R^2$ is 2,2-dimethylcyclopropyl, and R³ is alkyl of 1-15 carbon atoms, even more preferably R³ is alkyl of 1-5 carbon atoms. The most preferred species of inhibitor presently is that in which R³ is C₅ alkyl, R² is 2,2-dimethylcyclopropyl, and R¹ is hydrogen or sodium. This compound is Z-2-(2,2-dimethylcyclopropanecarboxamido)-2-octenoic acid, or sodium salt.

The most preferred administration route is parenteral, and the most preferred dosage form of the sodium Z-2-(2,2-dimethylcyclopropanecarboxamido)-2-octenoate with crystalline N-formimidoyl thienamycin is 75 or 150 mg of the former and 150 mg of the latter, coadministered by IV sterile aqueous solution injection, 3 or 4 times daily per human.

What is claimed is:

1. Crystalline N-formimidoyl thienamycin monohydrate, having the following X-ray powder diffraction:

| Peak Position | | Intensity | Peak Position | | Intensity |
|---|---|---|---|---|---|
| 2-Θ (CuKα) | d-Spacing (Å) | $I/I_o$ | 2-Θ (CuKα) | d-Spacing (Å) | $I/I_o$ |
| 9.75 | 9.07 | 100 | 26.9 | 3.31 | 75 |
| 11.35 | 7.80 | 40 | 28.7 | 3.11 | 37 |
| 13.85 | 6.39 | 11 | 29.9 | 2.99 | 17 |
| 14.5 | 6.11 | 4 | 30.8 | 2.90 | 7 |
| 15.75 | 5.63 | 14 | 31.85 | 2.81 | 12 |
| 17.5 | 5.06 | 30 | 32.6 | 2.75 | 10 |
| 18.9 | 4.69 | 27 | 32.9 | 2.72 | 10 |
| 19.6 | 4.53 | 12 | 33.4 | 2.68 | 5 |
| 20.0 | 4.44 | 14 | 33.9 | 2.64 | 10 |
| 21.45 | 4.14 | 30 | 34.8 | 2.58 | 26 |
| 21.75 | 4.08 | 36 | 35.6 | 2.52 | 14 |
| 22.3 | 3.98 | 45 | 37.0 | 2.43 | 5 |
| 22.9 | 3.88 | 30 | 38.3 | 2.35 | 9 |
| 23.3 | 3.82 | 28 | 39.3 | 2.29 | 6 |
| 24.3 | 3.66 | 33 | 40.0 | 2.25 | 9 |
| 25.35 | 3.52 | 24 | 42.0 | 2.20 | 14 |
| 25.8 | 3.45 | 20 | 42.4 | 2.14 | 18 |

* * * * *